(12) United States Patent
Daghighian

(10) Patent No.: US 12,721,581 B2
(45) Date of Patent: Sep. 1, 2026

(54) MULTI-MODALITY PROBE SYSTEM

(71) Applicant: Nicole Daghighian, New York, NY (US)

(72) Inventor: Nicole Daghighian, New York, NY (US)

(*) Notice: Subject to any disclaimer, the term of this patent is extended or adjusted under 35 U.S.C. 154(b) by 96 days.

(21) Appl. No.: 18/668,205

(22) Filed: May 19, 2024

(65) Prior Publication Data

US 2024/0382167 A1 Nov. 21, 2024

Related U.S. Application Data

(60) Provisional application No. 63/467,837, filed on May 19, 2023.

(51) Int. Cl.

| | |
|---|---|
| ***A61B 6/00*** | (2024.01) |
| ***A61B 5/00*** | (2006.01) |
| ***A61B 5/06*** | (2006.01) |
| ***A61B 6/42*** | (2024.01) |
| ***A61B 6/46*** | (2024.01) |
| ***A61B 6/50*** | (2024.01) |
| ***A61B 8/00*** | (2006.01) |
| ***A61B 8/08*** | (2006.01) |

(52) U.S. Cl.

CPC .......... *A61B 6/4411* (2013.01); *A61B 5/0071* (2013.01); *A61B 5/06* (2013.01); *A61B 6/4258* (2013.01); *A61B 6/4405* (2013.01); *A61B 6/4417* (2013.01); *A61B 6/461* (2013.01); *A61B 6/502* (2013.01); *A61B 6/54* (2013.01); *A61B 8/0825* (2013.01); *A61B 8/0833* (2013.01); *A61B 8/085* (2013.01); *A61B 8/4416* (2013.01); *A61B 8/4427* (2013.01); *A61B 8/461* (2013.01); *A61B 8/54* (2013.01)

(58) Field of Classification Search

CPC .... A61B 8/5261; A61B 6/4258; A61B 6/5247
See application file for complete search history.

(56) References Cited

U.S. PATENT DOCUMENTS

| | | | | |
|---|---|---|---|---|
| 11,039,803 | B1 * | 6/2021 | Butani | A61B 6/4258 |
| 12,228,689 | B2 * | 2/2025 | Yarnall | A61B 6/4057 |

(Continued)

*Primary Examiner* — Colin T. Sakamoto
(74) *Attorney, Agent, or Firm* — MASCHOFF BRENNAN; Paul G. Johnson

(57) ABSTRACT

A detection multimodality probe system for use in an operating room environment is provided. The system comprises a handheld multimodality probe for at least lesion detection providing Tc99 and I-125 modalities that receives installation of an RFID detection component embedded in a solid-state photomultiplier and scintillator unit of the probe. The system also receives installation of a fluorescence detection component at an end area of the probe. The system also receives installation of ultrasound, Magseed®, and white light camera functionality. The probe providing access to modalities comprising Tc99, I.125 modality, RFID, fluorescence, ultrasound and Magseed® enables a physician in an operating room to alternate between modalities without a need to change physical devices. The probe is connected to a control unit displaying results of the probe's operations on a screen in the operating room, a layout of the displayed results configurable according to preferences of a user of the probe.

19 Claims, 10 Drawing Sheets

(56) References Cited

U.S. PATENT DOCUMENTS

| | | | | |
|---|---|---|---|---|
| 2013/0172739 | A1* | 7/2013 | Paladini | A61B 6/5247 601/2 |
| 2014/0303486 | A1* | 10/2014 | Baumgartner | A61B 5/055 600/414 |
| 2015/0305700 | A1* | 10/2015 | Wendler | A61B 6/4417 600/436 |
| 2018/0210188 | A1* | 7/2018 | Ganapati | A61B 1/0638 |
| 2018/0303445 | A1* | 10/2018 | Subramanian | A61B 6/563 |
| 2019/0384048 | A1* | 12/2019 | Valdes | G02B 21/36 |
| 2020/0100741 | A1* | 4/2020 | Caballero Ontanaya | A61B 8/463 |
| 2021/0186465 | A1* | 6/2021 | Yeom | A61B 8/5207 |
| 2023/0280577 | A1* | 9/2023 | Valdes | G02B 21/06 600/476 |
| 2024/0164732 | A1* | 5/2024 | Farsoni | G01T 1/161 |
| 2025/0191586 | A1* | 6/2025 | Butani | G10L 15/22 |

* cited by examiner

MULTI-MODALITY PROBE SYSTEM

CROSS REFERENCE TO RELATED APPLICATIONS

The present non-provisional patent application is related to U.S. Provisional Patent Application No. 63/469,837 filed May 19, 2023, the contents of which are incorporated herein in their entirety.

FIELD OF THE DISCLOSURE

The present disclosure is in the field of surgical probes. More particularly, the present disclosure provides systems and method of installing a plurality of modalities into a handheld probe comprising Tc-99, I-125, RFID, fluorescence, magnetic surgical markers such as Magseed®, ultrasound, and visible light detector for imaging the field of view and displaying at least results of each modality on a monitor viewable by the surgeon using the probe.

BACKGROUND

Removal of suspect lesions in early-stage cancers is often assisted by wire localization or radioactive seed localization. Probes used to find lesions in the body for cancer include gamma probes, magnetic seed localization probes, and Radio Frequency Identification (RFID) probes. Each of these devices consumes space in the operating room.

For a lesion within a breast to be removed during a surgical procedure such as lumpectomy or biopsy, the lesion's location must be identified. Surgeons have various techniques to locate breast lesions that are both two-dimensional and three-dimensional. Three-dimensional procedures include radioactive seed localization and RFID. Both involve inserting a small consumable "tag" into the breast lesion with the aid of mammography or ultrasound prior to surgery, and during the surgery with aide of a handheld detector, the surgeon will detect these tags and through them the lesion during surgery.

Tracers are playing an increasingly important role in enhancing surgical precision. Tracers come in various forms, each offering unique advantages depending on the surgical scenario. Surgical procedures have become increasingly precise thanks in part to the use of specialized tracers. Tracers highlight specific tissues or structures, guiding surgeons and enhancing the accuracy of minimally invasive techniques. Below is a summary of commonly used tracers and their detection systems:

Technetium-99 (Tc-99): This radioactive tracer plays a vital role in nuclear medicine scans performed before and during surgery. Tc-99 attaches to molecules that target specific tissues. Tc-99 can be used in cancer surgery to identify tumors or sentinel lymph nodes, the first lymph nodes to receive drainage from a tumor.

Surgeons use a gamma probe to detect the gamma rays emitted by Tc-99, guiding the surgeon to detect the sentinel nodes in the axilla of the patient. The sentinel nodes are sent to pathology and help with mapping and staging of the patient's cancer.

Iodine-125 (I-125): Another radioactive tracer, Iodine-125, is often injected into the patient's tumors, and assists in identifying lesions.

Radio Frequency Identification (RFID) tags: Transitioning to the realm of intraoperative guidance, RFID tags offer real-time tracking during surgery. These tiny tags, often no larger than a grain of rice, can be attached to tissues. A handheld scanner emits radio waves that the tags respond to, revealing their precise location. This technology is particularly beneficial in minimally invasive procedures, where surgeons have limited visual access to the operative field.

Fluorescence imaging has been increasingly utilized in lesion detection during surgery, particularly in oncological and neurosurgical procedures. Primary uses of fluorescence in lesion detection during surgery include tumor visualization in which fluorescent dyes or probes may be administered to the patient prior to surgery. These dyes specifically target cancer cells or tumor-associated biomarkers. When illuminated with an appropriate light source, such as a near-infrared laser, the cancerous tissue fluoresces or illuminates, allowing surgeons to more rapidly visualize and accurately delineate tumor margins.

Fluorescence imaging is also used in sentinel lymph node mapping. During procedures involving the removal of lymph nodes, such as in breast cancer or melanoma surgeries, fluorescent dyes are injected near the tumor site. These dyes migrate to the sentinel lymph nodes, which are the first nodes to receive drainage from the tumor. By using fluorescence imaging, surgeons can identify and selectively remove these sentinel lymph nodes, reducing the risk of unnecessary lymph node dissection.

Fluorescence imaging distinguishes healthy tissue from diseased tissue during surgery. By targeting specific biomarkers associated with disease, fluorescent probes can highlight areas of abnormal tissue, allowing surgeons to precisely remove diseased tissue while preserving healthy surrounding tissue.

Fluorescence imaging provides real-time assessment of tissue perfusion. In surgeries where tissue perfusion is critical, such as vascular or reconstructive surgeries, fluorescence imaging can provide real-time assessment of blood flow. Indocyanine green (ICG) is a fluorescent dye commonly used for this purpose. By injecting ICG into the bloodstream, surgeons can monitor tissue perfusion by visualizing the fluorescence intensity in the target tissue, helping to guide surgical decisions and optimize outcomes.

In neurosurgery, fluorescence-guided imaging can aid in the visualization and resection of brain tumors, particularly gliomas. Tumor cells often infiltrate surrounding healthy brain tissue, making it challenging to distinguish tumor margins. Fluorescent dyes targeting tumor-specific biomarkers can help surgeons identify tumor boundaries more accurately, reducing the risk of leaving behind residual tumor tissue.

Overall, fluorescence imaging offers valuable advantages in lesion detection during surgery, including improved visualization of tumor margins, enhanced precision in tissue resection, and real-time assessment of tissue perfusion. As technology continues to advance, fluorescence-guided surgery is expected to play an increasingly important role in improving surgical outcomes across various medical specialties.

Multiple modalities are often needed during different phases of surgery. For example, the surgeon may require a handheld RFID detector to locate the RFID tag that was left inside the tumor during mammography or ultrasonography. Also, for the localization of the sentinel lymph node labeled by a radiotracer such as Tc-99m sulfur colloid, the surgeon utilizes another hand-held detector of gamma ray.

When surgeons are removing a tumor lesion with the use of an I-125 radioactive seed, they can often use a gamma detection probe. The same probe they already intend to use for sentinel node mapping later in the surgical procedure.

However, if the surgeon chooses to use RFID for their procedure, he or she would need another probe in the operating room. This would mean another apparatus to have in the sterile field and insert into the patient.

Existing technologies include detector probes for at least: 1) Tc-99m isotope that emit 140 keV gamma rays for sentinel node biopsy, 2) I-125 isotope in the form of seed for tumor localization, 3) radio wave antenna for localization of the RFID tags for tumor localization, 4) mini-camera or detector for fluorescent detection of immunofluorescent dye for various tissue characterization such as blood perfusion, 5) Ultrasound transducer for ultrasound imaging, 6) visible light detector for imaging the field of view, 7) magnetic field detectors for localizing magnetic surgical markers such as Magseed®.

DETAILED DESCRIPTION

Figure 1A:
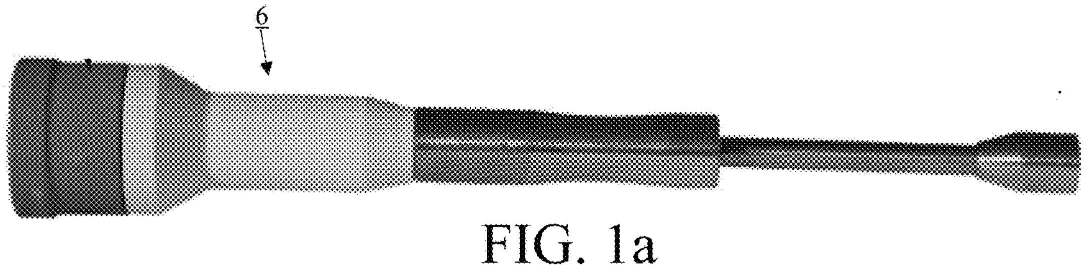
FIG. 1*a* is an image of a multi-modality probe according to an embodiment of the present disclosure.

The present disclosure provides a hand-held probe that combines multiple modalities in one assembly and provides utility to the surgeon and promotes efficiency in the operating room in general. Systems and methods described herein provide a surgical probe for use in an operating room environment with a multitude of modalities, all available on the single handheld device.

All or some of the seven modalities mentioned in the Background section above become available to a user of the probe on a single physical device. Software and other functionality executing on the probe and on a control unit computer allows the user to alternate between these modalities by manipulating controls on the probe.

Alternatively, a clinician operating the control unit computer may handle the task of alternating between modalities upon instruction of the surgeon in the operating room. The user need not even set the probe down as the single device allows access to all or some of the seven modalities via the activated controls.

Which modality or modalities a surgeon chooses to use, the manner and order in which he/she uses them, and how the results of the surgeon's use of the modalities are displayed on the screen in the operating room may vary from one surgeon to the next, based on each surgeon's preferences and the specifics of the surgical operation. In embodiments some surgeons may never use one or more modality. Each of these factors also depends on the type of treatment being administered, based on the patient's treatment plan determined by their care team.

Further, the probe with its up to seven modalities is modular such as hardware and software for each modality may be changed out or not installed at all. It is not mandatory that the probe provided herein be outfitted to contain components for all seven modalities. Some surgeons may never want a particular modality and therefore components for that unwanted modality may never be installed in the probe used by those surgeons.

The handheld probe with its seven available modalities communicates with the nearby control unit computer. The computer directs how results of examinations using the various modalities and other information are projected on a large monitor. The monitor may be in the operating room for viewing by a physician that is using the probe.

In embodiments, the control unit may be operated by a clinician separate from the surgeon but in communication with the surgeon. In embodiments, the surgeon may verbally or electronically instruct the clinician to change the modality of the probe instead of making the change him/herself.

A probe that can detect various radioisotopes, RFID, florescent light, take optical images, perform ultrasonograph and detect Magseed® or other magnetic surgical markers may allow surgeons to detect multiple types of lesions through only one device in the operating room. The surgeon is provided significant flexibility and convenience by not having to alternate between physical handheld devices.

The intraoperative probe provided herein may detect a combination of Tc-99 for sentinel lymph node biopsy, I-125 seed localization and RFID. The probe will allow surgeons to have more choices on breast lesion localization methods without the concerns of cost for the hospital of additional devices or sterilization hazards.

Many gamma probes can detect a combination of Tc99m for sentinel lymph nodes and tumor through I-125 filled seeds. By being able to detect Tc-99m, 1-125 and RFID, the number of instruments needed by the surgeon during a cancer localization and resection comprising mastectomy or lumpectomy will be reduced, saving vital space in the operating room.

The hospital staff will only need to switch between modalities in software on the control unit screen instead of changing from one physical probe to another.

The probe provided herein with its seven available modalities connects with the control unit computer that may be situated in the surgical environment or elsewhere. A clinician accessing the computer manipulates how data gathered by the probe and its modalities is displayed on a large monitor in the operating room or on other devices.

The system may, for example, permit various arrangements of data generated by the various modalities depending on preferences of a surgeon or other professional using the probe in a surgical setting.

A circuit board is integrated into the probe for the detection modalities and is programmed to alternate between the modalities based on selection by clinician and based on control unit selection. Communication between the circuit board contained within the probe and the control unit computer may be via Bluetooth. The probe has a solid-state photomultiplier detection system for radioactive tracers (Tc-99 and I-125). Tungsten shielding is in place that houses the detection systems for radioactive tracers to maintain a straight spatial resolution from radioactive emissions.

An RFID detection system installed in the probe connects to the circuit board in the probe. The probe communicates with the control unit that displays radiofrequency intensity and distance in millimeters. The magnetic seed detection system in the probe is housed in metallic shielding to avoid electromagnetic interference.

As noted, the probe also contains a system for ultrasound detection. The ultrasound system comprises a transducer array, a beamformer, and a digital signal processor. A white light camera lens is available to display a live image if desired.

A fluorescence detector is located in a front area of the probe without tungsten shielding. The front window fluorescence detector must be transparent to absorb light for fluorescence detection and not interfere with gamma detection.

Figure 1B:
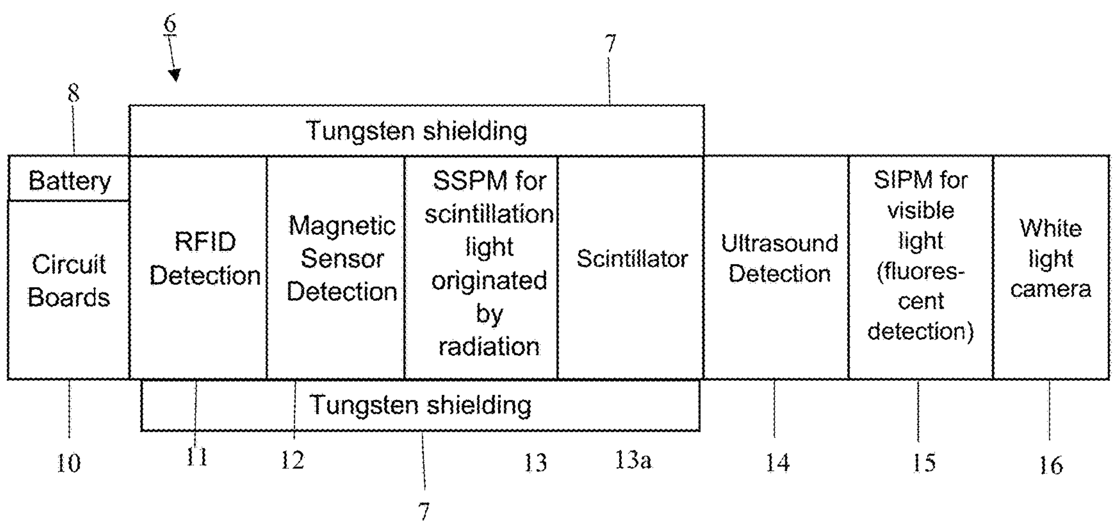
FIG. 1*b* is a block diagram of a system of a multi-modality probe according to an embodiment of the present disclosure.

Turning to the figures, FIG. 1*a* and FIG. 1*b* illustrate components and interactions of a system 100, specifically the probe and its components as described above. FIG. 1*a* illustrates the exterior of the probe 6 with the wider portion of the probe to the left of the device being the area held by the user.

FIG. 1*b* is a block diagram illustrating the modalities and other components of the system provided herein. Components of the probe 6 illustrated include a battery 8, circuit boards 10, an RFID Detection system 11, a magnetic sensor detection system 12, SiPM-sintillator for radiation detection 13, scintillator 13*a,* ultrasound detection 14, SiPM for fluorescent light 15, and a white light camera 16. Tungsten shielding 7 also covers components as illustrated in FIG. 1*b*. The acronym sspm or SiPM both indicate solid-state photomultiplier.

Figure 1C:
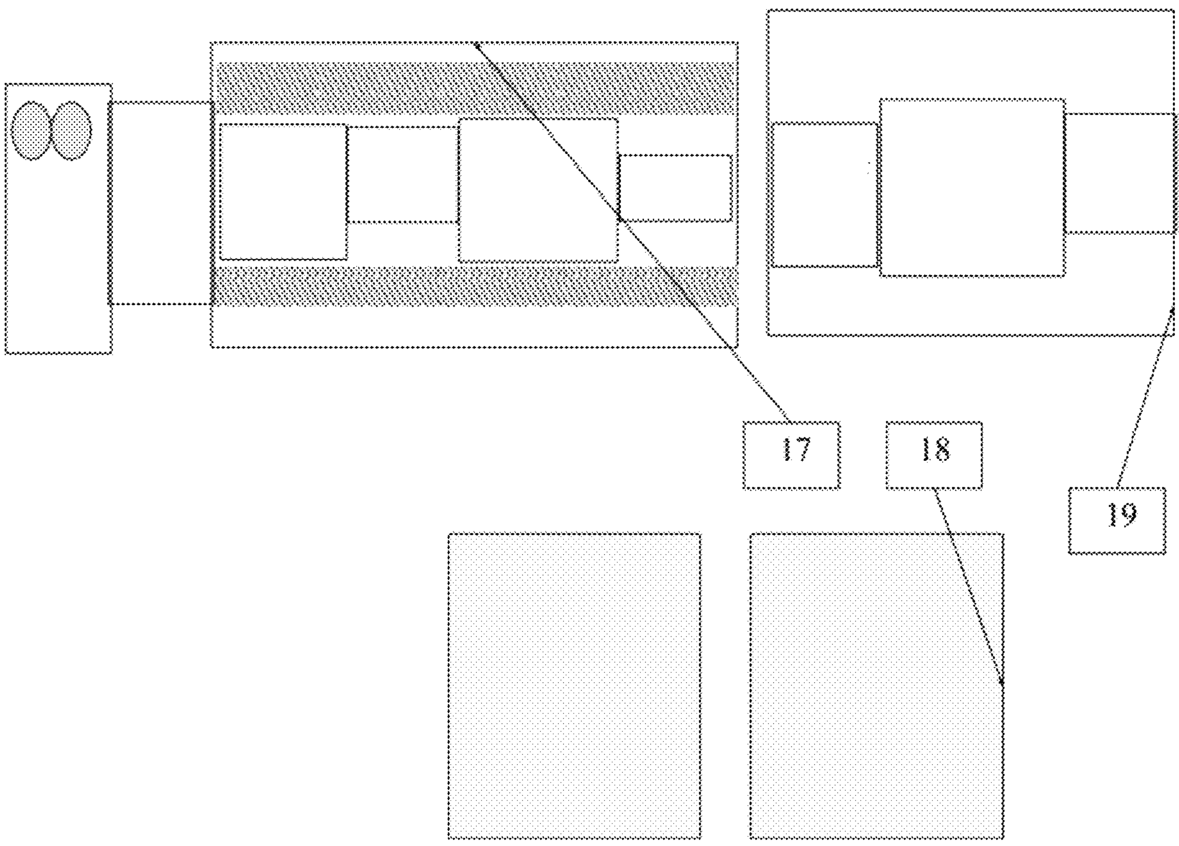
FIG. 1*c* is an image of a display provided by a system of a multi-modality probe according to an embodiment of the present disclosure.

FIG. 1*c* illustrates a locking mechanism, specifically the component with label 17 which is a locking mechanism on the main body of the probe that can seamlessly attach and reattach systems for ultrasound, florescence and white light camera to the main body of the probe. This brings utility for clinicians to have a smaller probe diameter size based on the case since ultrasound, florescence and white light detectors may increase the probe's diameter. This type of locking mechanism may conserve sterilizations. For example, there will be a recess for locking with regular/known methods. This could also be through fitting connectors that can make contact with relevant circuitry in the probe. Component 18 is a cross section of locking mechanism. Discussion herein of locking mechanism does not mean that such mechanism must be part of the system. Such mechanism is optional.

Figure 2:
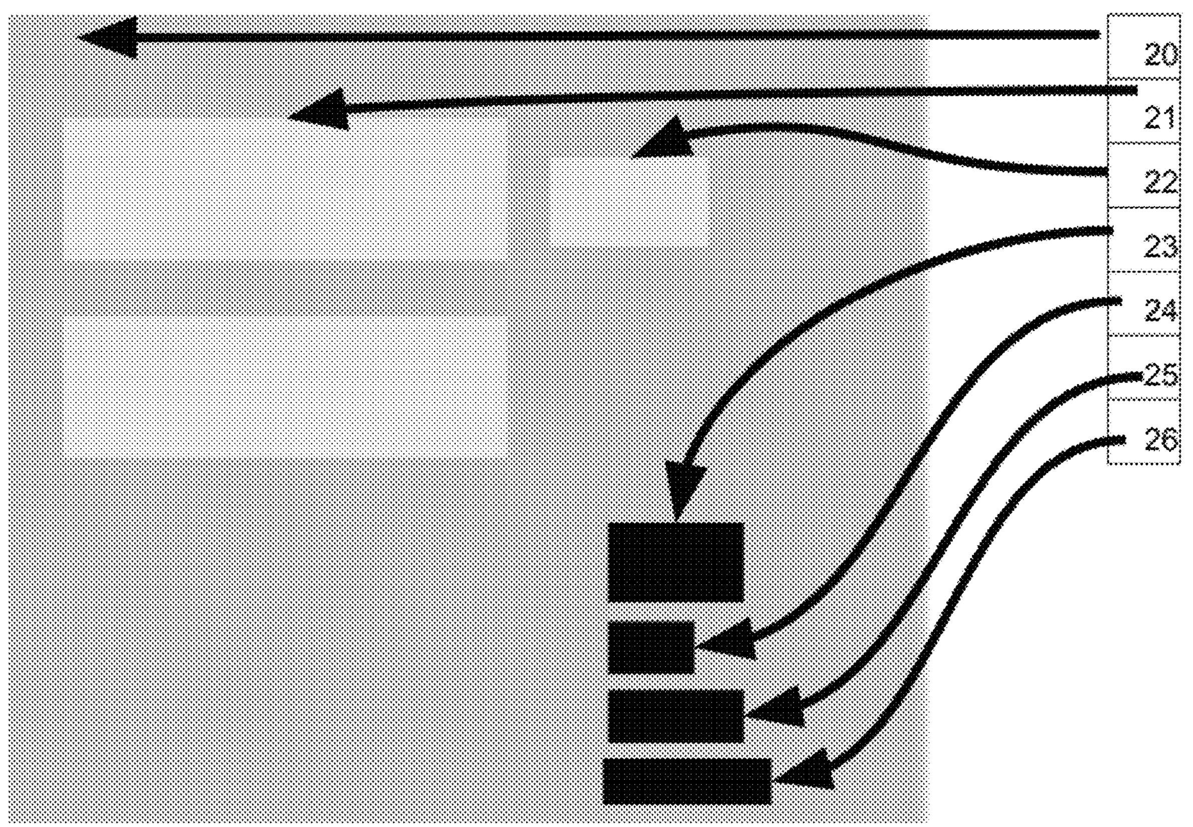
FIG. 2 is an image of a display provided by a system of a multi-modality probe according to an embodiment of the present disclosure.

FIG. 2 is a depiction of a screen of the control unit computer described above wherein an operator may manipulate views as selected by surgeons' operating room staff. Control unit screen, indicated by the label 20, displays array of count intensities from the probe depending on clinician choice. Since gamma probes are most often used during breast tumor detection and removal and sentinel node biopsies, the default intensity count displays may be Tc-99 and I-1-25. Features that are typical for these devices include but are not limited to sonification, accumulate 10 second, background count subtract, and sound zero level.

The component of FIG. 2 indicated by label 21 is an intensity count display for the I-125 SEED. Selection of this object enables a clinician to select to display intensity counts of radioactive seed and distance from seed in millimeters or other measure. Components indicated hereafter as buttons may be objects that when selected invoke functionality. Buttons may be icons, links or other objects.

Label 22 indicates a display for distance reading in mm for tumor detection. This is the distance count for either I-125 or RFID depending on the mode that is set by the clinician in the settings which is based on the black buttons. Label 23 of FIG. 2 indicates an icon or button for clinicians to quickly simplify the screen by showing "primary counts" for the case. This could be only a set of one or two counts that are displayed.

Label 24 of FIG. 2 is an icon or button for the clinician to access a graphical menu that enables selection for immunofluorescence image display, intensity counts, or further customization of displays. For example, the clinician may enter a selection for a screen that displays all four types of intensity counts (Tc-99, I-125, RFID, and immunofluorescence) and a live image of the green immunofluorescence intensity, or any other permutations thereof.

Label 25 indicates a control enabling display for count intensity. Label 26 of FIG. 2 may be a button for distance readings to switch from I-125 seed localization to RFID instantaneously. Label 26 may be a button on control unit for clinician to switch from "RFID" readings to I-125 seed localization for breast lesion and/or tumor detection.

Figure 3:
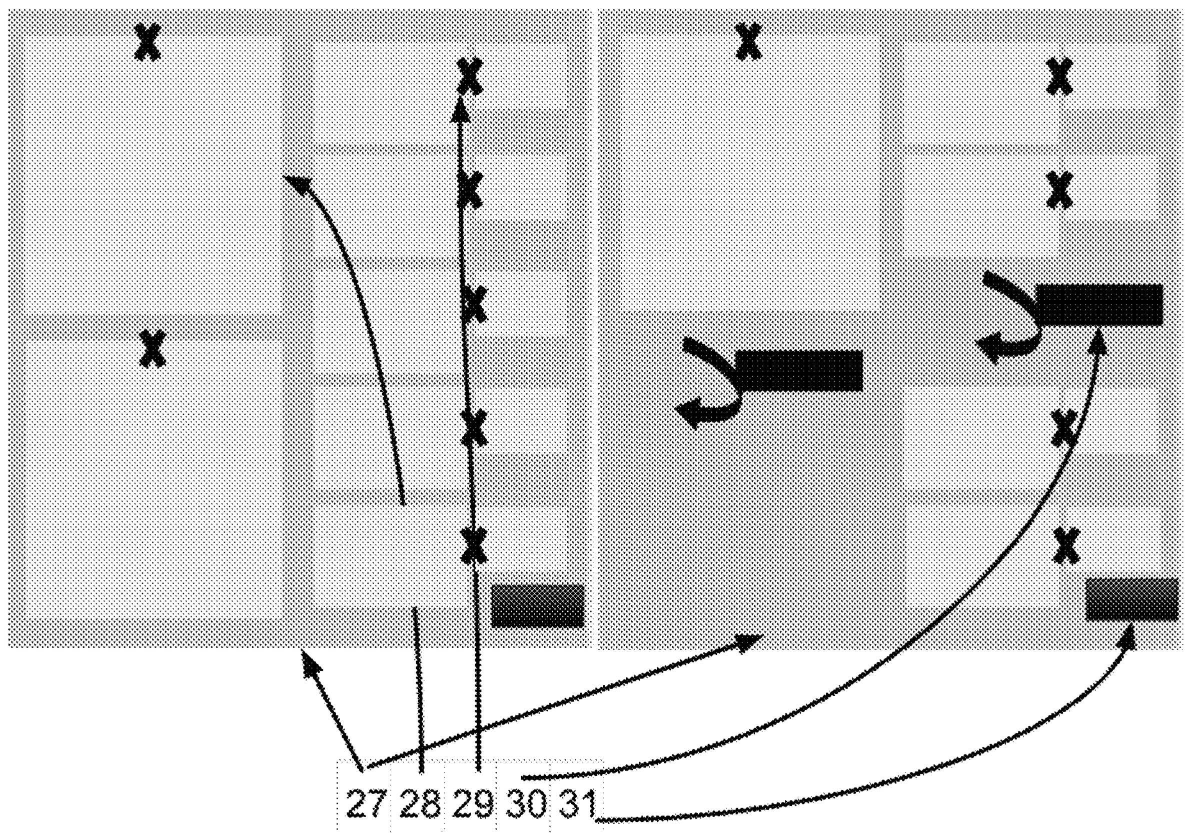
FIG. 3 is an image of a display provided by a system of a multi-modality probe according to an embodiment of the present disclosure.

FIG. 3 is an image of screens of the control unit viewable by a clinician when assisting a surgeon using the multimodality probe. Label 27 is for the control unit screen displaying intensity count readings in small rectangles on the right. Smaller boxes on the far right are corresponding distance measurements if the modalities displayed involve that measurement (RFID and I-125). Label 28 represents green immunofluorescence intensity displayed as an image. Live images may be displayed either in the form of tc-99 heat maps, ultrasound, white light, IFG or superimposition thereof.

Label 29 in FIG. 3 is a button or other selectable object for clinicians to stop display of intensity counts. Label 30 is a button for clinicians to redo the display they stopped. Label 31 is a button for clinicians to return to a different interface with more details of certain intensity count displays such as Tc-99 which includes background count subtract and sound zero level, or the energy setup form for the radioactive tracers.

Figure 4:
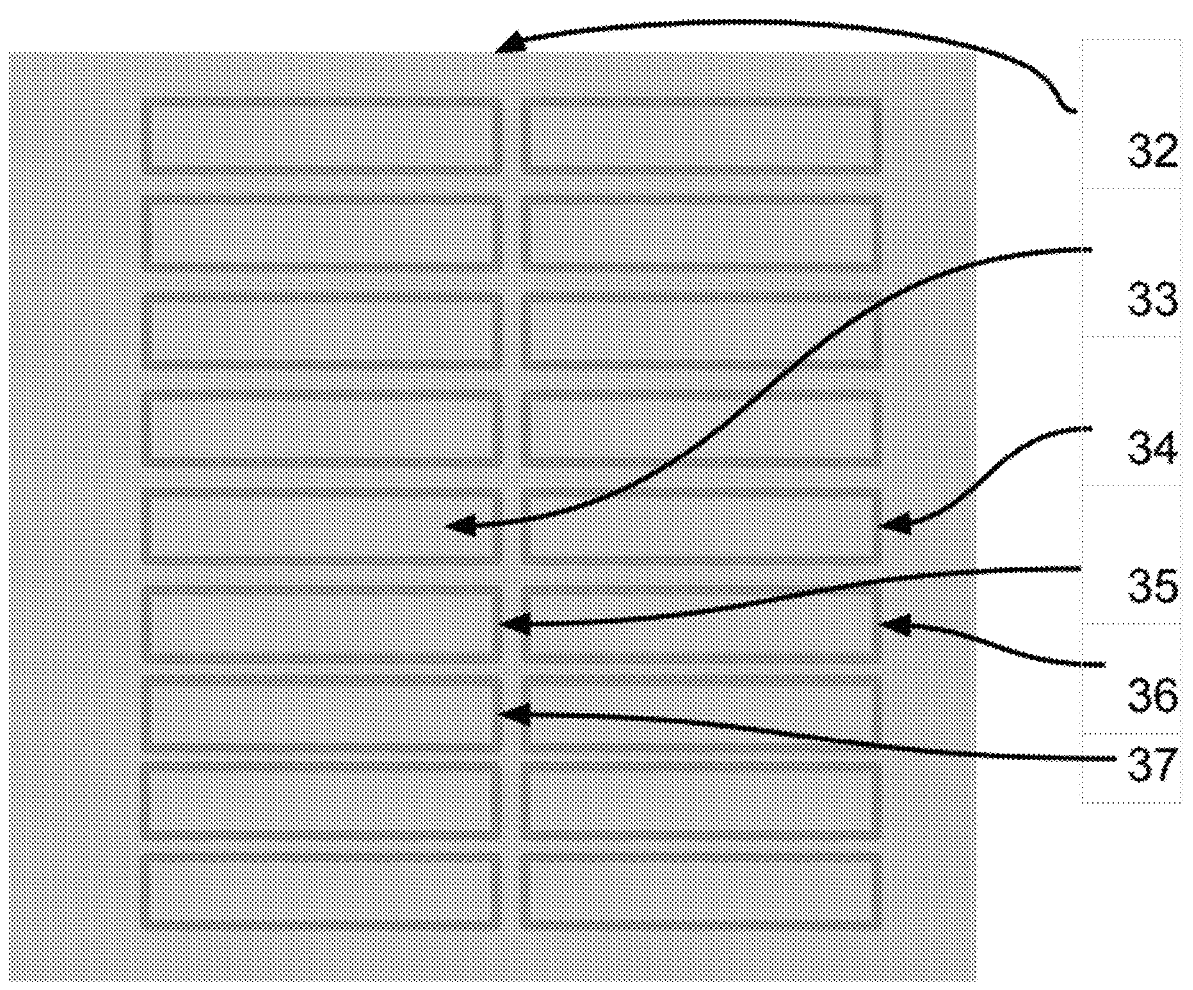
FIG. 4 is an image of a display provided by a system of a multi-modality probe according to an embodiment of the present disclosure.

FIG. 4 is a view of a display provided in various embodiments for customizing settings for the control unit computer for switching user interface in settings in response to preference indicated by surgeons or other users. Label 32 is an image of a control unit screen illustrating different display settings. Label 33 is a button for clinicians to configure sounds for RFID signal detection and modulation.

Label 34 is a button for clinicians to configure sounds for magnetic surgical marker (e.g., Magseed®) signal detection and modulation. Label 35 is a button for clinicians to open window for immunofluorescence green intensity display as an image. Label 36 is a button for immunofluorescence intensity display as counts. Label 37 is a button for clinicians to customize layout of intensity displays as counts or image.

Figure 5:
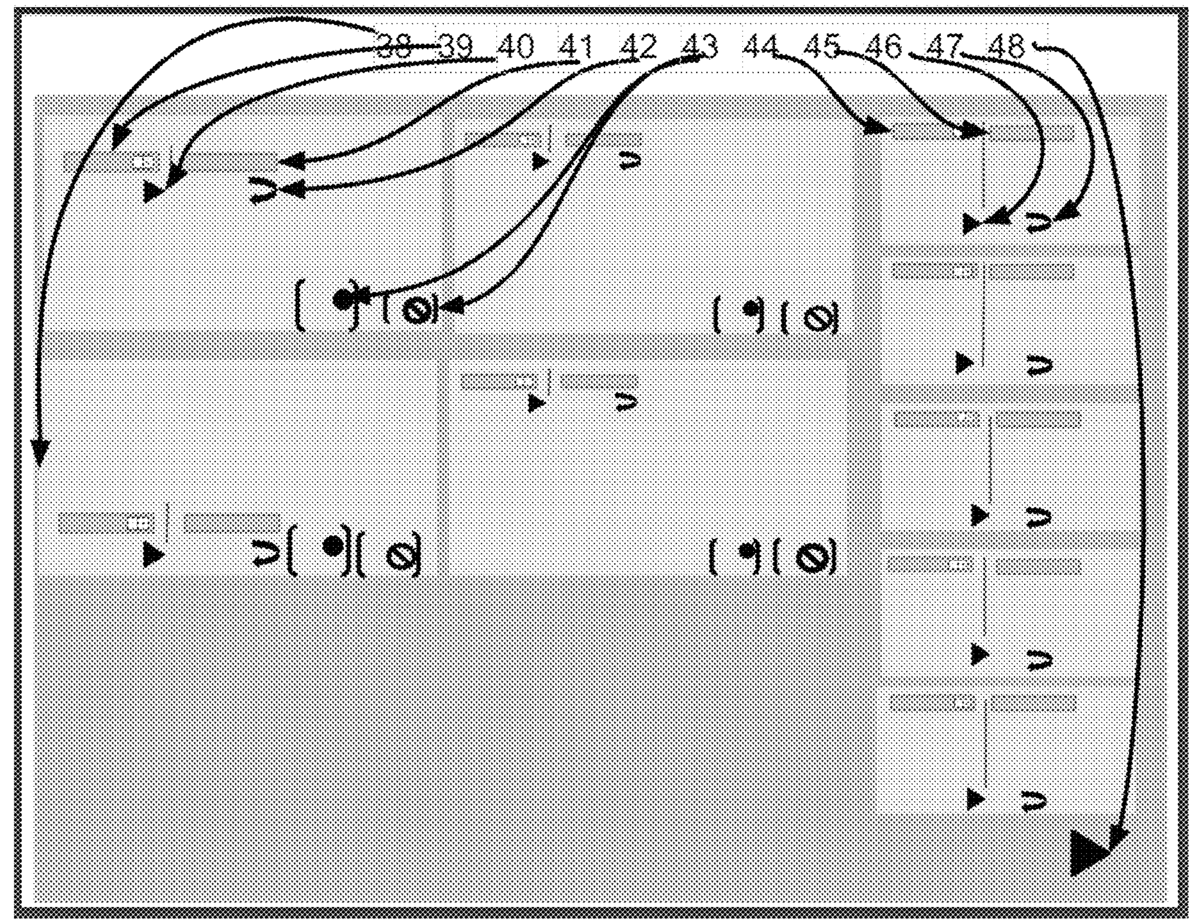
FIG. 5 is an image of a display provided by a system of a multi-modality probe according to an embodiment of the present disclosure.

FIG. 5 is another view of displays provided by the control unit computer as it exchanges messages with the probe. Label 38 is a customization page for clinicians to select which modality is displayed on each panel from top to bottom. FIG. 5 mimics the appearance of the display as viewed by a clinician.

FIG. 5 depicts all alternatives available to the surgeon. Viewing the display as shown in FIG. 5, the surgeon sees the alternatives available to him/her. In embodiments, objects appearing in the display may be superimposed atop one another. Two-dimensional object intensity images such as Tc-99, IFG and white camera may be superimposed atop one another, but not when ultrasound is involved.

Label 39 is a button for clinicians to select display image type on screen. These options are ultrasound, tc-99 intensity display, immunofluorescent green display, white light display or images displaying both simultaneously displaying and superimposed to each other. For example, the surgeon can superimpose the white light visual with a tc-99 intensity display or white light visual superimposed with an immunofluorescent green display, or white light, tc-99 intensity display and immunofluorescent green display. all superimposed at once.

Label 40 is a button to confirm the selection for that intensity image modality for that display panel in the control unit. Label 41 is an example of image writing the modality type on the other side confirming the selection of the clinician for the given display panel. Label 42 is a button for clinicians to undo selection. Text on other side will disappear to confirm the undoing of the selection and will allow the clinician to select another modality for that display panel from the dropdown.

Label 43 is a notice to clinician that display is auto recorded upon detection with a cancel option button for any intensity displays as images. Label 44 illustrates options for modalities that clinicians can select to display on the control unit. Clinicians can select this as a button, and it will display the options as a dropdown. The options include Tc-99, I-125, RFID, magnetic surgical marker (e.g., Magseed®) and Immunofluorescence green.

Label 45 is a button to confirm the selection for that modality for that display panel in the control unit. Label 46 is an image of writing the modality type on the other side confirming the selection of the clinician for the given display panel.

Label 47 illustrates a button for clinician to undo selection. Text on other side will disappear to confirm the undoing of the selection and will allow the clinician to select another modality for that display panel from the dropdown. Label 48 is a button to confirm the preferences for the clinician and move to the screen with the displays in the preferred order. FIG. 5 is where clinician makes decision for control unit display for case based on treatment/procedure for patient.

Figure 6:
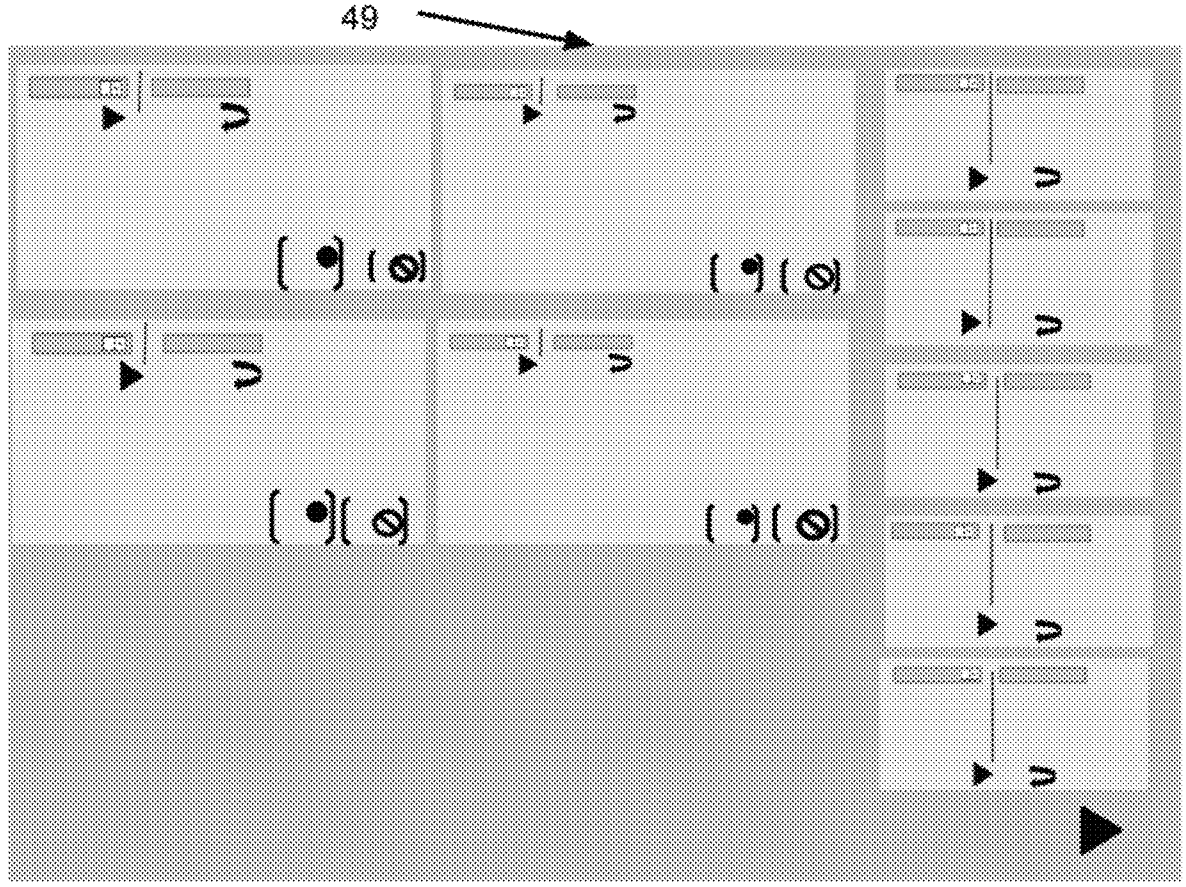
FIG. 6 is an image of a display provided by a system of a multi-modality probe according to an embodiment of the present disclosure.

FIG. 6, also indicated by label 49, is an image of a display illustrating an embodiment of a clinician making the following settings in customization page: Tc-99 intensity display, Immunofluorescent Green, and white camera superimposed on the top left, the ultrasound image displayed on the top right and the white camera displayed on the bottom left. Count screens for Tc-99m and RFID are displayed.

Figure 7:
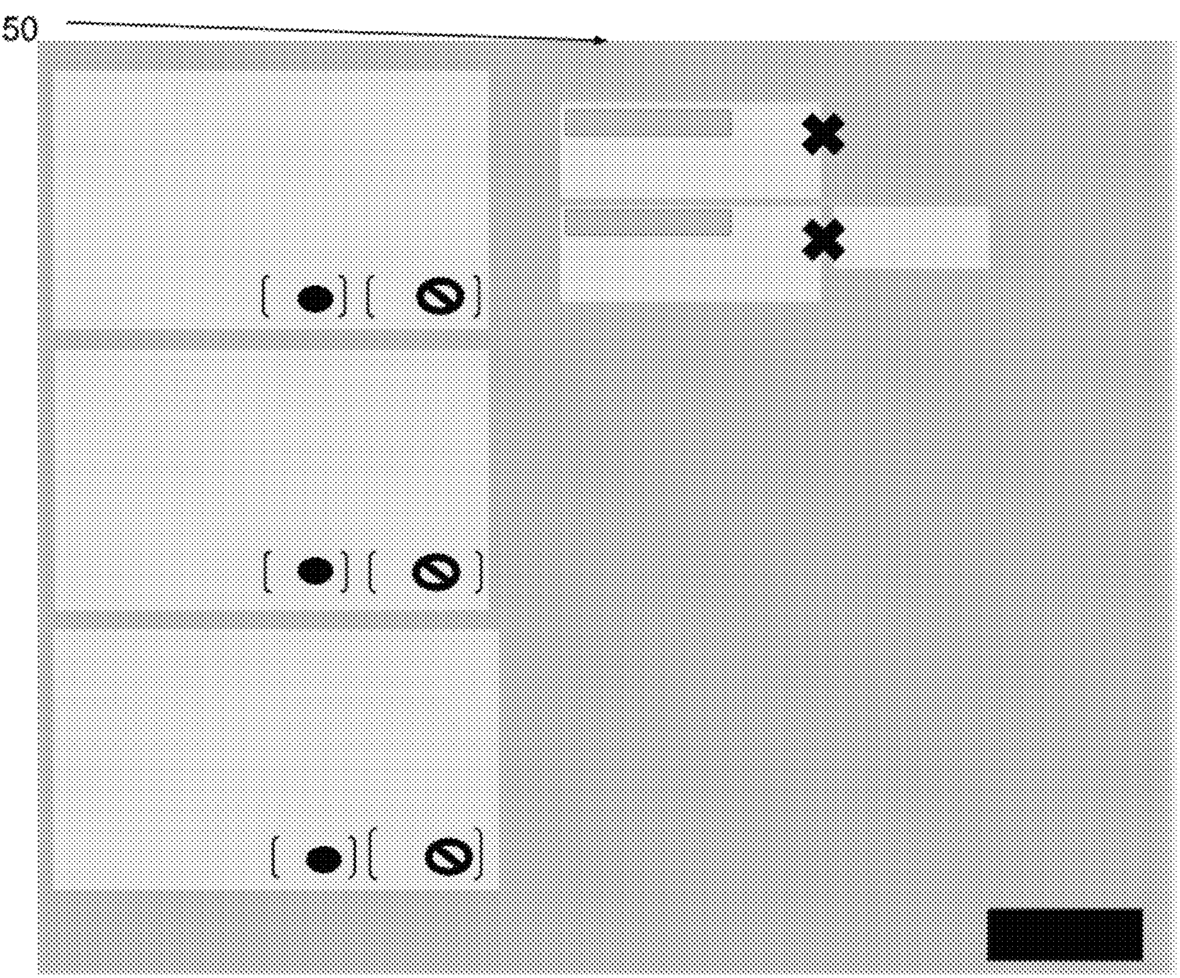
FIG. 7 is an image of a display provided by a system of a multi-modality probe according to an embodiment of the present disclosure.

FIG. 7, also indicated by label 50, is an image of a display illustrating an embodiment of customized displays from previous examples, now in operational mode in FIG. 7.

Figure 8:
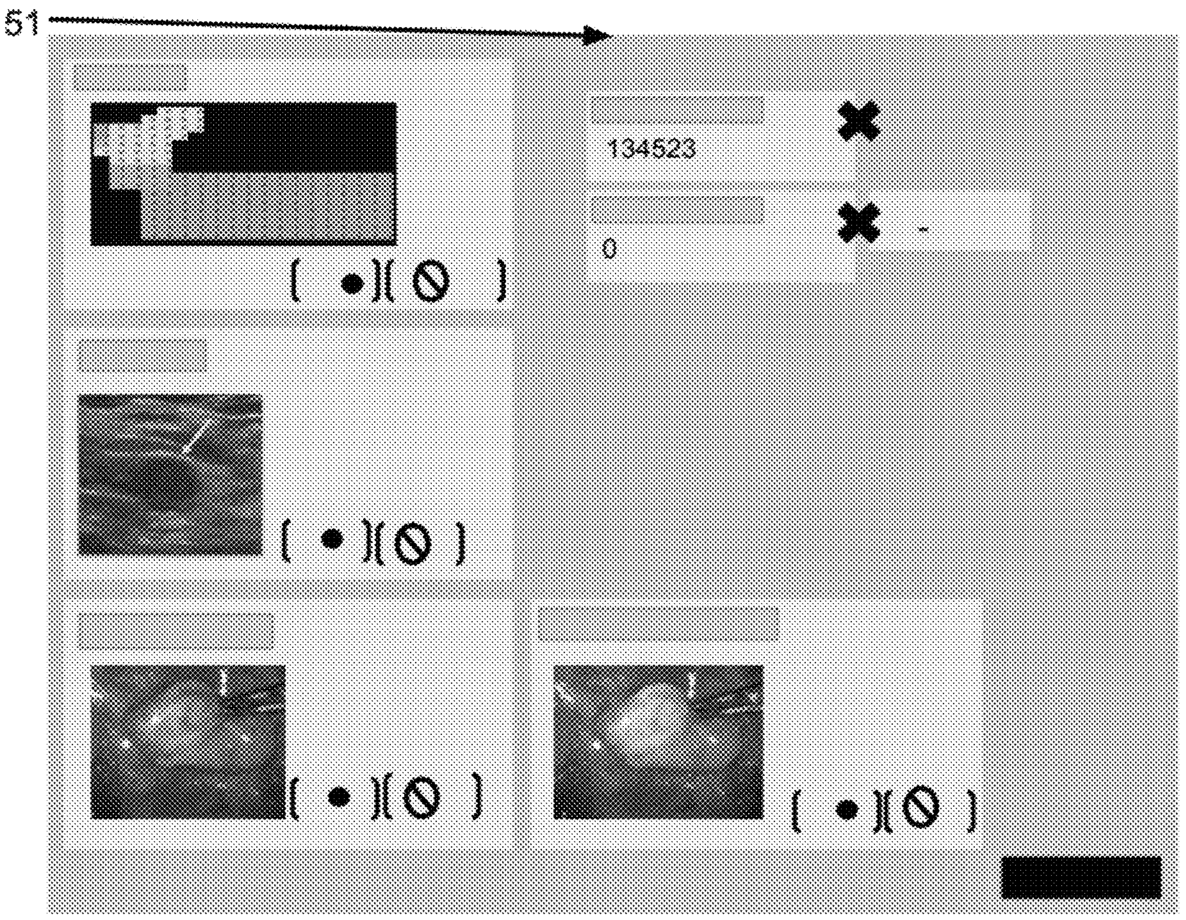
FIG. 8 is an image of a display provided by a system of a multi-modality probe according to an embodiment of the present disclosure.

FIG. 8, also indicated by label 51, is an image of a display illustrating an embodiment of a clinician making settings in customization to utilize Tc-99m intensity display, ultrasound, immunofluorescent green intensity and white camera as well as counts for RFID and Tc-99m. The screen on the right is an embodiment of the probe being in use and being near a sentinel lymph node. Since the intensity displays that were selected can help characterize/localize sentinel nodes an image is displayed. In FIG. 8, the Tc-99m count is high because the probe is next to a sentinel lymph node where Tc-99m has a large amount of uptake. Since the probe is not near the cancer lesion where RFID tags are placed, there is no intensity count for RFID and the distance box on the right has "-" written since the probe is not within the radius of localization of the cancer lesion.

Figure 9:
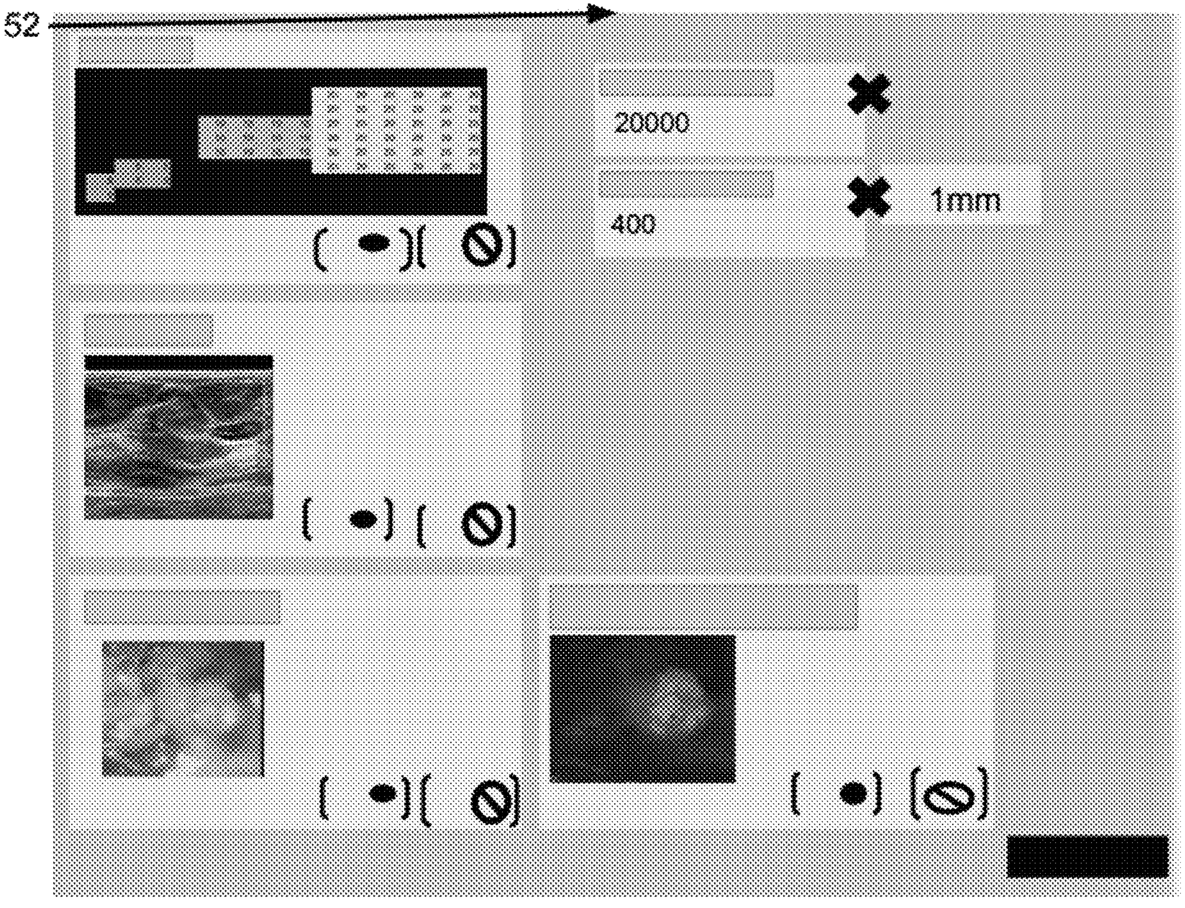
FIG. 9 is an image of a display provided by a system of a multi-modality probe according to an embodiment of the present disclosure.

FIG. 9, also indicated by label 52, is an image of a display illustrating an embodiment of a clinician now on a cancer tumor that has an RFID chip located and visible through the ultrasound display. A tumor is also visible in white light camera, RFID and Tc-99mintensity since the patient had the tumor injected with Tc-99m. Counts for Tc-99mare also displayed. RFID counts are also on display as well as distance measurement from the RFID chip that guides surgeons to excise the tumor.

In an embodiment, a detection multimodality probe system for use in an operating room environment is provided. The system comprises a handheld multimodality probe for at least lesion detection providing Tc99 and I-125 modalities that receives installation of an RFID detection component embedded in a solid-state photomultiplier and scintillator unit of the probe. The system also receives installation of a fluorescence detection component at an end area of the probe. The system also receives installation of ultrasound, a magnetic surgical marker (e.g., Magseed®) detector, and white light camera functionality.

The probe providing access to six modalities comprising Tc99, I.125 modality, RFID, fluorescence, ultrasound and magnetic surgical marker (e.g., Magseed®) enables a physician in an operating room to alternate between modalities without a need to change physical devices. The probe is connected to a control unit that displays results of the probe's operations on a screen in the operating room, a layout of the displayed results configurable according to preferences of a user of the probe.

The system provides functionality, via the control unit associated with the probe, for a user to select to display intensity counts of radiofrequency methods for breast lesion and tumor detection. The probe contains a circuit board integrated for the detection modalities and programmed to alternate between the modalities based on user selection at the control unit, communication between the circuit board and the control unit via at least Bluetooth.

The RFID detection component connects via the circuit board to the control unit that configures display of both radiofrequency intensity and distance in millimeters. The modalities are interchangeable and hardware and software associated with each modality is subject to installation or removal without affecting other modalities presently installed in the probe. The fluorescence detector component is installed in a front of the probe without tungsten shielding and wherein a front window of the probe is transparent to absorb light for fluorescence detection and to not interfere with gamma detection.

In another embodiment, a multimodality probe and control unit is provided comprising a handheld multimodality probe for use in a surgical environment. The system also comprises a control unit supporting the probe. The system also comprises a customization application executing on the unit that receives a first message from the probe in an operating room, the first message containing data describing tissue observed by the probe. The system also receives a second message indicating at least one of a switching of modalities, based at least on the received second message, changes an order of panels on a display screen in the operating room. Each panel is associated with a modality and displays at least data generated by the modality. The probe and control unit include IFG display as image, Tc-99 intensity displayed as image, include white light camera, include images wherein the images are at least partially superimposed, and further include images with ultrasound displayed separately but simultaneously.

Changing of the order is based on direction of a physician using the probe. The modalities comprise Tc-99, I.125, RFID, fluorescence, ultrasound, and magnetic surgical marker (e.g., Magseed®). The panels display at least an array of count intensities from the probe depending on user choice.

Default intensity displays are for Tc-99 and I.125 modalities based on projected use during tumor detection and removal and sentinel node biopsies. The control unit provides a first object entitled "I-125 SEED" promoting selection of display intensity counts of radioactive seed and distance from seed in millimeters. The control unit provides a second object, selection of which causes display of intensity counts of radiofrequency method for at least one lesion where RFID disposable is inserted into the patient.

In yet another embodiment, a method for displaying electronic content collected by a probe device in a surgical environment is provided. The method comprises a control unit computer receiving data from a handheld multimodality probe in an operating room. The method also comprises the computer, based on receiving a first instruction, activating a display device in the operating room. The method also comprises the computer, based on receiving a second instruction, directing the device to display intensity of immunofluorescence green. The method also comprises the computer, based on receiving a third instruction, displaying the intensity as counts. The method also comprises the computer, based on receiving a fourth instruction, discontinuing displaying the intensity as counts and commencing displaying the intensity as at least one image.

The method also comprises the multimodality probe observing tissue using one of Tc-99, I.125, RFID, fluorescence, ultrasound, and magnetic surgical merker (e.g., Magseed®) technologies installed in the probe. The method also comprises the computer enabling transition to a different interface with more details of a displayed intensity count.

A displayed intensity count is associated with Tc-99 technology and comprises at least one of background count subtract and sound zero level and energy setup form for radioactive tracers. The method also comprises the computer confirming display preferences of a clinician for order of technologies and transitioning to a screen with displays in the confirmed preferred order.

The invention claimed is:

1. A detection multimodality probe system for use in an operating room environment, comprising:

a handheld multimodality probe for at least lesion detection providing Tc99 and I-125 modalities, the probe comprising:

an RFID detection component embedded in a solid-state photomultiplier and scintillator unit of the probe, a fluorescence detection component at an end area of the probe, and ultrasound, magnetic surgical marker, and white light camera functionality.

2. The system of claim 1, further comprising a control unit coupled to the probe, the control unit configured to display results of the probe's operations on a screen in the operating room, a layout of the displayed results configurable according to preferences of a user of the probe.

3. The system of claim 2, wherein the system provides functionality, via the control unit associated with the probe, for a user to select to display intensity counts associated with Tc-99, I-125, RFID, and immunofluorescence methods for breast lesion and tumor detection.

4. The system of claim 2, wherein the probe contains a circuit board integrated for the detection modalities and programmed to alternate between the modalities based on user selection at the control unit, communication between the circuit board and the control unit via at least Bluetooth.

5. The system of claim 4, wherein the RFID detection component connects via the circuit board to the control unit that configures display of both radiofrequency intensity and distance in millimeters.

6. The system of claim 1, wherein the modalities are interchangeable and hardware and software associated with each modality is subject to installation or removal without affecting other modalities presently installed in the probe.

7. The system of claim 1, wherein the fluorescence detector component is installed in a front of the probe without tungsten shielding and wherein a front window of the probe is transparent to absorb light for fluorescence detection and to not interfere with gamma detection.

8. A multimodality probe and control unit, comprising:

a handheld multimodality probe for use in a surgical environment;

a control unit supporting the probe; and a customization application executing on the unit that:

receives a first message from the probe in an operating room, the first message containing data describing tissue observed by the probe, receives a second message indicating at least one of a switching of modalities, based at least on the received second message, changes an order of panels on a display screen in the operating room, each panel associated with a modality and displaying at least data generated by the modality, wherein the probe and control unit are configured to display, on a display coupled to the control unit, one or more of immunofluorescence green (IFG) images, Tc-99 intensity images, white light camera images, at least partially superimposed images, or ultrasound images.

9. The system of claim 8, wherein changing of the order is based on a direction of a physician using the probe.

10. The system of claim 8, wherein the modalities comprise Tc-99, I.125, RFID, fluorescence, ultrasound, and magnetic surgical marker.

11. The system of claim 8, wherein the panels display at least an array of count intensities from the probe depending on user choice.

12. The system of claim 8, wherein default intensity displays are for Tc-99 and I-125 modalities based on projected use during tumor detection and removal and sentinel node biopsies.

13. The system of claim 8, wherein the control unit provides a first object entitled "I-125 SEED" promoting selection of display intensity counts of radioactive seed and distance from seed in millimeters.

14. The system of claim 8, wherein the control unit provides a second object, selection of which causes display of intensity counts associated with Tc-99, I-125, RFID, and immunofluorescence methods for at least one lesion where RFID disposable is inserted into the patient.

15. A method for displaying electronic content collected by a probe device in a surgical environment, comprising:

receiving, by a control unit computer, data from a handheld multimodality probe in an operating room;

activating, by the control unit computer and based on receiving a first instruction, a display device in the operating room;

directing, by the control unit computer and based on receiving a second instruction, the display device to display intensity of immunofluorescence green;

displaying, by the control unit computer and based on receiving a third instruction, the intensity as counts; and discontinuing displaying, by the control unit computer and based on receiving a fourth instruction, the intensity as counts and commencing displaying the intensity as at least one image.

16. The method of claim 15, further comprising the multimodality probe observing tissue using one of Tc-99, I-125, RFID, fluorescence, ultrasound, and magnetic surgical marker technologies installed in the probe.

17. The method of claim 15, further comprising the control unit computer enabling transition to a different interface with more details of a displayed intensity count.

18. The method of claim 17, wherein the displayed intensity count is associated with Tc-99 technology, the method further comprising displaying the details of the displayed intensity count including at least one of background count subtract and sound zero level and energy setup form for radioactive tracers.

19. The method of claim 15, further comprising the computer confirming display preferences of a clinician for order of technologies and transitioning to a screen with displays in the confirmed preferred order.

* * * * *